United States Patent
Lowe

[19]

[11] Patent Number: 6,159,158
[45] Date of Patent: Dec. 12, 2000

[54] DIAGNOSTIC CATHETER SYSTEM FOR NASOPHARYNGEAL OBSTRUCTIONS

[76] Inventor: Michael W. Lowe, 1920 High Dr., Liberty, Mo. 64068

[21] Appl. No.: 09/348,195

[22] Filed: Jul. 6, 1999

[51] Int. Cl.[7] ...................................................... A61B 5/08
[52] U.S. Cl. ............................................. 600/529; 604/50
[58] Field of Search ..................................... 600/529, 587, 600/593, 532; 128/204.23, 897; 604/27, 50, 54

[56] References Cited

U.S. PATENT DOCUMENTS

| | | |
|---|---|---|
| 3,410,264 | 11/1968 | Frederik . |
| 3,721,228 | 3/1973 | Prediger et al. . |
| 4,444,201 | 4/1984 | Itoh . |
| 4,584,998 | 4/1986 | McGrail ............................ 128/207.15 |
| 4,790,327 | 12/1988 | Despotis . |
| 4,844,085 | 7/1989 | Gattinoni . |
| 5,046,491 | 9/1991 | Derrick . |
| 5,099,845 | 3/1992 | Besz et al. . |
| 5,203,343 | 4/1993 | Axe et al. . |
| 5,257,636 | 11/1993 | White . |
| 5,291,897 | 3/1994 | Gastrin et al. . |
| 5,313,955 | 5/1994 | Rodder . |
| 5,335,656 | 8/1994 | Bowe et al. . |
| 5,477,860 | 12/1995 | Essen-Moller . |
| 5,513,637 | 5/1996 | Twiss et al. . |
| 5,555,890 | 9/1996 | Schaller . |
| 5,704,345 | 1/1998 | Berthon-Jones . |
| 5,730,129 | 3/1998 | Darrow et al. . |
| 5,803,066 | 9/1998 | Rapoport et al. . |
| 5,810,741 | 9/1998 | Essen-Moller . |
| 5,836,302 | 11/1998 | Homuth et al. . |
| 5,954,050 | 9/1999 | Christopher ........................ 128/204.23 |

*Primary Examiner*—Cary O'Connor
*Assistant Examiner*—Navin Natnithithadha
*Attorney, Agent, or Firm*—Shughart Thomson & Kilroy P.C.

[57] ABSTRACT

An apparatus and method for identifying and marking regions of tissue obstruction in the upper airway of a patient. The invention provides a greatly improved method for use during a sleep apnea study to particularize the location of a region of obstruction. The precise location of the obstruction may be marked for surgical removal or reduction. Broadly speaking, the apparatus includes a multiluminate catheter having an outer wall circumscribed by multiple discrete perforate regions. The proximal portion of each lumen opens into a selected perforate region and the distal portion is coupled with a pressure transducer. Each lumen is equipped with a syringe port for injecting a tissue marking dye into the obstructing tissue region. The catheter outer wall may include a radiopaque marker in order to facilitate location of the catheter within the airway of a patient.

23 Claims, 2 Drawing Sheets

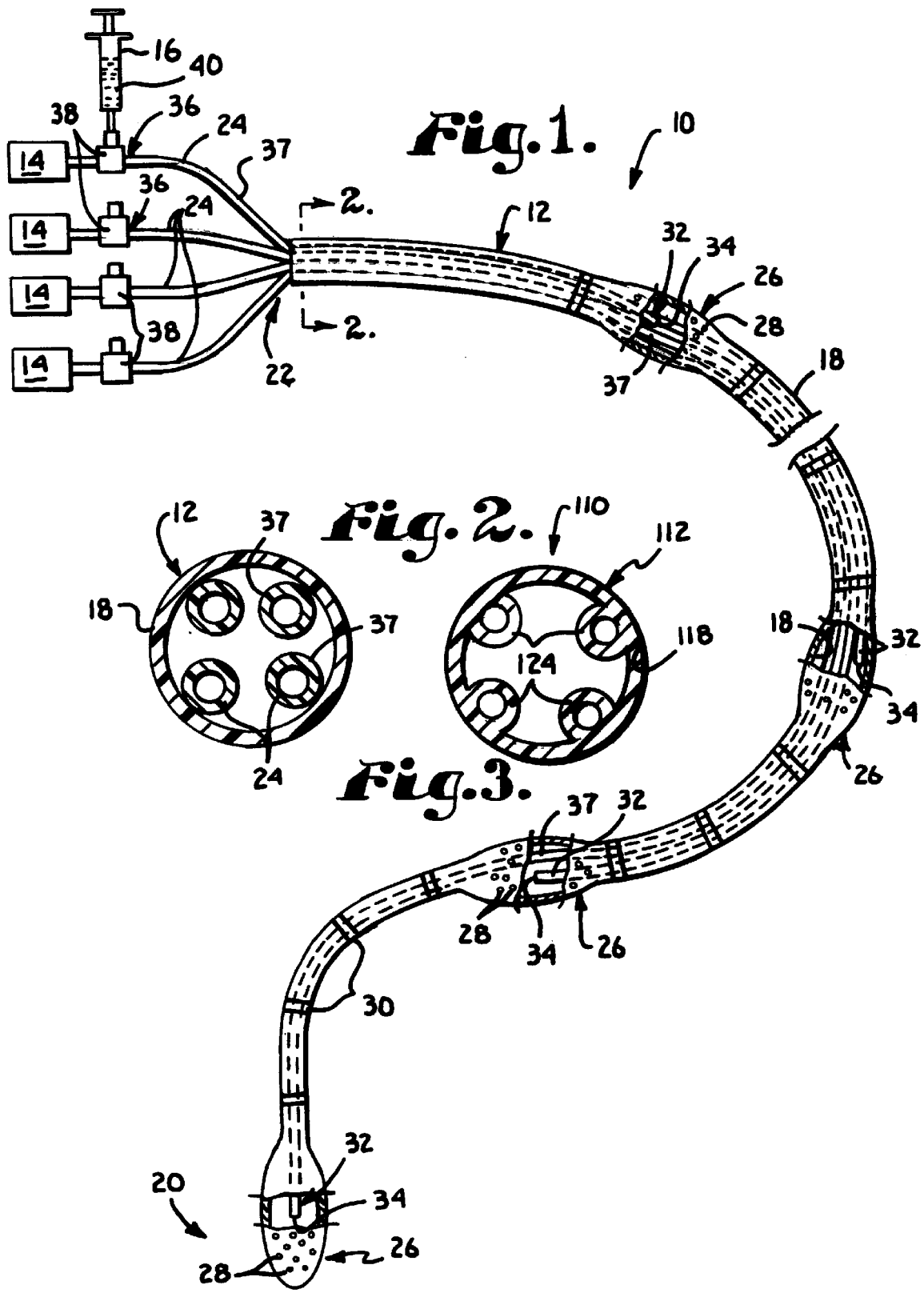

DIAGNOSTIC CATHETER SYSTEM FOR NASOPHARYNGEAL OBSTRUCTIONS

BACKGROUND OF THE INVENTION

1. Field of the Invention

The present invention is broadly concerned with an apparatus and method for locating and marking regions of obstruction in the upper airway of a patient. More particularly, it is concerned with a multiluminate catheter having an outer wall circumscribed by a plurality of discrete perforate regions. Each lumen is coupled at one end with one of the perforate regions, and at the other end with a pressure transducer for measuring pressure changes in the lumen which indicate the presence of a region of obstruction. Each lumen is equipped with a syringe port for injecting a dye marker through the lumen and outwardly through the perforate region and into the obstructed regions, and the outer catheter wall includes a radiopaque marker for determining the placement of the catheter in situ.

2. Description of the Related Art

Obstructive Sleep Apnea Syndrome, (OSA Syndrome) is a respiratory disorder characterized by periodic cessation of breathing caused by upper airway obstruction. The primary consequences of OSA Syndrome are episodic asphyxia and sleep fragmentation. More than 30,000 patients seek treatment for OSA Syndrome each year. The most common clinical features of the syndrome are heavy snoring and daytime sleepiness. OSA Syndrome is a serious disorder and its consequences can be life-shortening. An association has been demonstrated between sleep apnea and increased risk of hypertension, myocardial infarction and stroke.

The etiology of the syndrome is obstruction of one or more portions of the upper airway. Sleep causes the muscles of the upper airway to relax and the associated soft tissues to sag, resulting in narrowing or collapse of the upper airway, and consequent reduction in ventilation. Although the diaphragm continues to contract and the contractions may even intensify, obstructive apnea may be observed in sleep studies as a cessation of the airflow at the nose and mouth.

The decreased ventilation causes a rise in carbon dioxide tension and a drop in oxygen saturation of the arterial blood. The entire body is affected, since oxygen delivery to the tissues may be reduced by as much as 60% during an episode of OSA.

A diagnosis of OSA syndrome is generally established through a polysomnographic study in a sleep laboratory. Such studies may include monitoring of brain activity by electroencephalography (EEG), eye movement by electrooculography, cardiac rhythm by electrocardiography, blood oxygen level by oximetry, airflow measurement at the nose and mouth, and measurement of inspiratory effort by inductance plethysmography, intraesophageal pressure measurement or surface electronmyography of the inspiratory muscles. The upper airway should be evaluated for structural problems as well, such as nasal polyposis, lymphomatous involvement of the nasopharynx, nasopharyngeal carcinomas and bone abnormalities.

Once obstructive sleep apnea syndrome is diagnosed, therapy includes correction of associated medical conditions, drug therapy and dietary management, mechanical aids and surgical intervention. Correction of the associated medical conditions may be aimed at the effects such as excessive daytime sleepiness or the consequences, such as right-sided heart failure. Such therapy is specific to the individual, and generally does not address the underlying causes of the apnea. In certain cases avoidance of provoking agents such as alcohol, sedatives and androgens may be effective. Where obesity is contributory, dietary management or gastric stapling may be employed to achieve sustained weight loss. Drug therapy has been shown to be of only limited effectiveness in treating OSA.

Mechanical aids, such as Continuous Positive Airway Pressure (CPAP) and Bilevel Positive Airway Pressure (BiPAP) are the most commonly employed therapy for management of obstructive sleep apnea. Nasal CPAP treatment involves placing a mask over the nose for use as a pneumatic splint, while a stream of air is pumped through the mask and into the patient's airway. BiPAP treatment involves additional independent programming of the inspiratory and expiratory pressures, so that the pressure is lowered during exhalation. Such devices may be extremely effective when used correctly and regularly. However, because they do not correct the underlying causes of obstructive sleep apnea, they must be used indefinitely.

Mechanical aids are also subject to poor patient compliance. About forty percent of patients are estimated to experience difficulty tolerating CPAP for prolonged periods of time. One of the problems associated with nasal CPAP is the bulk of the required equipment. Patient complaints include that the equipment comes off during sleep, that it causes dryness of the mucous membranes of the mouth and throat, and that it makes noise which keeps the sleeper or spouse awake.

Surgical therapy may be employed to improve airway patency through permanent alteration of the soft tissues. Surgical therapy is particularly effective where the obstruction is caused by uvulopalatal narrowing of the relaxed pharyngeal airway. The most commonly practiced procedures are palatal surgery such as uvulopalatopharyngoplasty (UPPP) and laser-assisted uvulopalatoplasty (LAUP), in which the tonsils, uvula, and portions of the soft palate and posterior pillars of the fauces are excised in order to widen the posterior pharynx behind the palate.

Despite the extensive nature of such surgical procedures, UPPP and LAUP are not effective in curing obstructive sleep apnea in about half of all cases. Other surgical procedures, such as nasal surgery, genioglossus tongue advancement, hyoid suspension, maxillomandibular advancement and tracheotomy are also available, and may be attempted when UPPP and LAUP have failed.

In order to make a differential diagnosis of OSA, to identify whether a patient may be a candidate for surgical therapy, and to determine the appropriate surgical procedure in the first instance, it is thus necessary to precisely identify the tissue region which causes narrowing or occlusion of the airway when the patient is at rest.

In the past, various attempts have been made to employ catheters to identify such areas within the upper airway. Such devices employ a flexible cannula, such as an endotracheal tube having an aperture at or near the end, coupled with an external pressure transducer. The catheter is inserted through one of the nares into the upper airway of a patient. When occlusion occurs, a drop in pressure is relayed by the transducer to a visual display. While such catheters may be employed to verify the existence of an occlusion somewhere within the airway, they do not serve to identify the location of the obstruction.

By using a pair of catheters to measure respiratory pressure and by gradually withdrawing one of the catheters until a pressure drop is registered, it is possible to identify the general area of a single region of occlusion. Graduated markings have been applied along the length of the catheter as an aid in approximating the location of an obstruction within the patient. However, occlusions which are caused or exacerbated by relaxation of the upper airway in OSA syndrome must be evaluated in a sleeping patient through polysomnography. The necessary manipulation of two catheters required by such methods renders them unsuitable for use during sleep apnea studies. In addition, identification of multiple regions of occlusion would require extensive catheter manipulation, which is likely to cause abrasion of the soft tissues of the upper airway and result in patient discomfort.

Attempts have been made to locate airway obstructions with a multiluminate catheter in which each lumen is coupled with an opening in the side of the catheter. However, such devices contain only a single opening in the catheter wall coupled with each lumen. These individual openings are subject to clogging by airway secretions, which may cause a false low pressure reading. Because of the length of the airway and limitation on the number of possible lumens by the catheter diameter, external catheter openings must be widely placed. Thus, even where the openings remain unclogged, they are unable to particularize the location of an obstructed region.

The apparatus and method of the present invention are specifically designed to employ during a sleep apnea study a single, stationary catheter to locate with particularity regions of obstruction in the airway of a patient. The obstructing tissue is then marked for surgical removal or reduction.

SUMMARY OF THE INVENTION

The present invention is directed to an apparatus and method for identifying and marking regions of tissue obstruction in the upper airway of a patient. The invention provides a greatly improved method for use during a sleep apnea study to particularize the location of a region of obstruction. The precise location of the obstruction may be marked for surgical excision. Broadly speaking, the apparatus includes a multiluminate catheter having an outer wall circumscribed by multiple discrete perforate regions. The distal portion of each lumen opens into a selected perforate region and the proximal portion is coupled with a pressure transducer. Each lumen is equipped with a syringe port for injecting a tissue marking dye into the obstructing tissue region. The catheter outer wall may include a radiopaque marker in order to facilitate location of the catheter within the airway of a patient.

OBJECTS AND ADVANTAGES OF THE INVENTION

The principal objects of the present invention are to provide a method and apparatus for diagnosing obstructions of the upper airway of a patient; to provide such an apparatus and method which can be used in a sleeping patient; to provide such an apparatus and method which employs a single, stationary catheter; to provide such an apparatus and method capable of identifying with particularity the location of an upper airway obstruction in a patient; to provide such an apparatus having a catheter having an outer wall circumscribing multiple lumens, each coupled with a pressure transducer for recording pressure changes; to provide such an apparatus having a single multiluminate catheter, each lumen coupled with a syringe port for introducing a marker dye into an identified area of obstructing tissue; to provide such an apparatus having an outer wall circumscribed by a plurality of perforate areas; to provide such an apparatus wherein the lumens are of varying lengths; to provide such an apparatus wherein each lumen is in fluidic communication with perforations in the outer wall; to provide such an apparatus wherein each perforate area includes a lumen terminal port; to provide such an apparatus wherein the outer circumscribing wall includes a terminal port area for each lumen; to provide such an apparatus which includes multiple perforated regions which are resistant to occlusion by secretions and encroachment of adjacent soft tissue; to provide such an apparatus which permits gaseous volumetric pressure changes to traverse perforated regions in the outer catheter wall; to provide such an apparatus having a plurality of lumens, each having an aperture coupled with a diaphragm or opening into a terminal port area; to provide such an apparatus which may be remotely located in the upper airway of a patient; to provide such an apparatus wherein the catheter wall includes a radiopaque marker substance; to provide such an apparatus having catheter and lumen surfaces coated with a non-stick coating; to provide a method for using such an apparatus during a patient sleep study by inserting the cannula through the nares of a patient and into the upper airway, measuring the pressure in a plurality of lumens, to identify areas of low pressure, injecting a dye material into lumens which demonstrate a pressure drop, and removing the catheter and excising or ablating or reducing areas of tissue which occlude the patient's airway during sleep; providing such an apparatus and method which are relatively easy to use, inexpensive to produce and particularly well-suited for their intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

BRIEF DESCRIPTION OF THE DRAWINGS

FIG. 1 is a perspective view of a diagnostic catheter system in accordance with the present invention, with parts broken away showing a lumen aperture disposed within each catheter terminal port region.

FIG. 2 is a cross section of the apparatus of FIG. 1, showing disposition of multiple lumens within the catheter.

FIG. 3 is a cross section of an alternate multiluminate catheter, showing disposition of the lumens within the catheter.

DETAILED DESCRIPTION OF THE INVENTION

Figure 5:
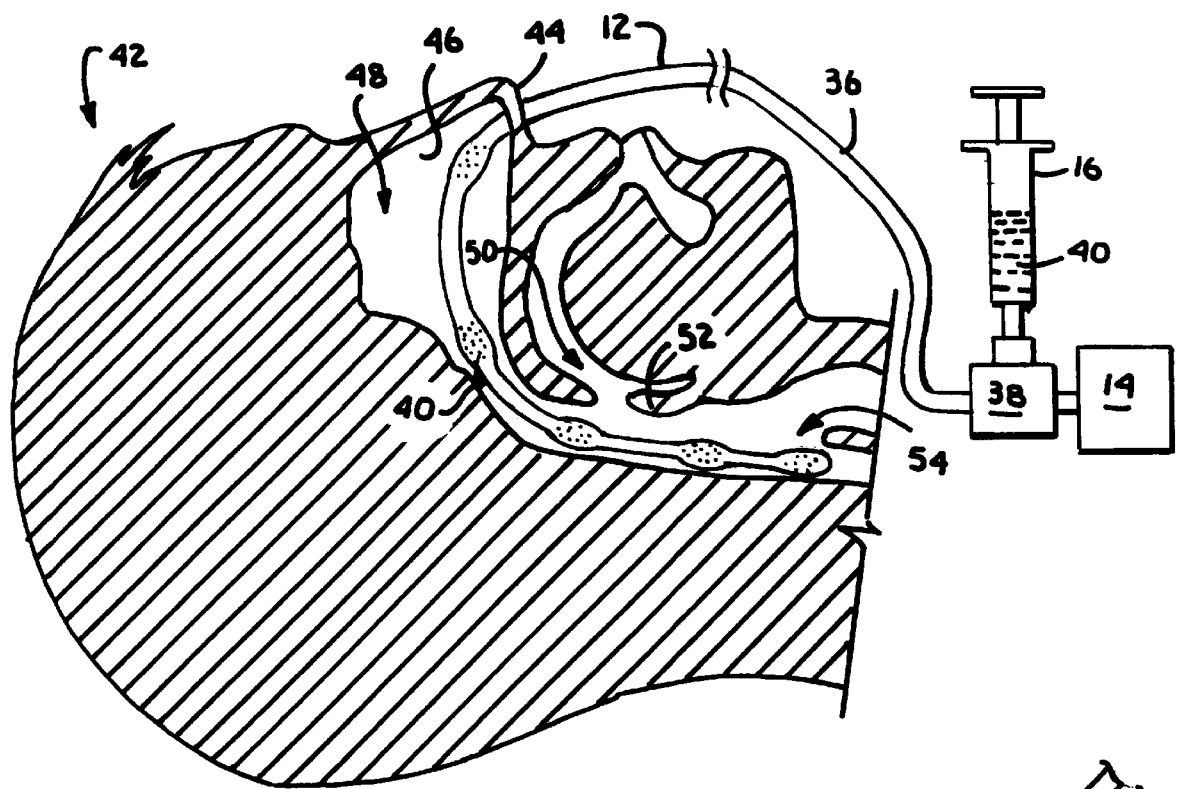
FIG. 5 is a diagrammatic cross section of a head and neck of a patient illustrating use of the apparatus of FIG. 1 in the upper airway of the patient, and depicting injection of a dye into a region of tissue obstruction.

As required, detailed embodiments of the present invention are disclosed herein; however, it is to be understood that the disclosed embodiments are merely exemplary of the invention, which may be embodied in various forms.

Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to FIG. 1, a diagnostic catheter system 10 for locating an obstruction in the upper airway of a patient in accordance with the invention broadly includes a catheter 12, coupled with pressure transducers 14, and a syringe 16. The catheter 12 includes a generally tubular outer wall 18 having a closed distal end 20, an proximal distal end 22, and circumscribing a plurality of lumens 24.

In more detail, the outer wall 18 includes at spaced intervals a series of perforate terminal port regions 26, defined by a number of small apertures 28 circumscribing the outer wall 18. The catheter 12 is preferably about 15 to about 25 centimeters in length, in order to permit placement within the entire upper airway of a patient. The catheter 12 may be constructed so that the perforate terminal port regions 26 are be spaced differentially along the length of the catheter 12, to correspond with regions of the airway of particular interest, e.g., with a concentration in the proximal intranasal, oropharyngeal, hypopharyngeal and supraglottic areas. It is formed of a flexible, non-toxic synthetic resinous material, such as polyurethane, silicone rubber or any other suitable material. The surfaces of the catheter outer wall 18 as well as the lumens 24 may be coated with a non-stick substance. The outer wall 18 may include a radiopaque substance 30 for fluoroscopic or radiographic location of the catheter in situ.

The lumens 24 are circumscribed in spaced relationship with each other by the catheter outer wall 18. Each lumen includes a distal end 32 having an aperture 34, a proximal end 36, and a generally tubular sidewall 37. The length of each lumen is predetermined, so that one lumen aperture 34 is in fluid communication with each catheter terminal port region 26. While the preferred lumen proximal end 32 terminates in an aperture 34, those skilled in the art will appreciate that the aperture 34 may also be located on the sidewall 37 adjacent to the proximal end 32.

The termination of one lumen 24 at each terminal port region 26 enables a reduction in the diameter of the catheter outer wall 18 after each terminal port region 26. In still other embodiments, the catheter 12 and its lumens 24 may be of equal length, with the distal lumen ends 32 terminating adjacent the distal catheter ends 20. However, in all embodiments the lumen apertures 34 are located in fluidic communication with the terminal port regions 26 of the catheter.

Each lumen proximal end 36 is coupled with a syringe port 38 and a pressure sensor device, such as a transducer 14. The components of a pressure measurement system are conventional and will not be described herein, but may be enumerated to include a display, power supply and connecting cables. The syringe port 38 is preferably threaded, to accept a Luer-type locking syringe 16. The syringe is charged with a nontoxic dye substance 40.

Like the catheter 12 the lumens 24 are constructed of a flexible, non-toxic synthetic resinous material. They may be colorless, or they may be pigmented with colors corresponding to various available dye colors, so that a different dye color may be injected into the corresponding color-coded lumen.

Another embodiment of the catheter system 110, depicted in FIG. 3 is similar in all respects except that the catheter outer wall 118 is of integral construction with the lumens 124, so that the lumens form a generally circular arrangement, the center of which is coaxial with the catheter 112.

Figure 4:
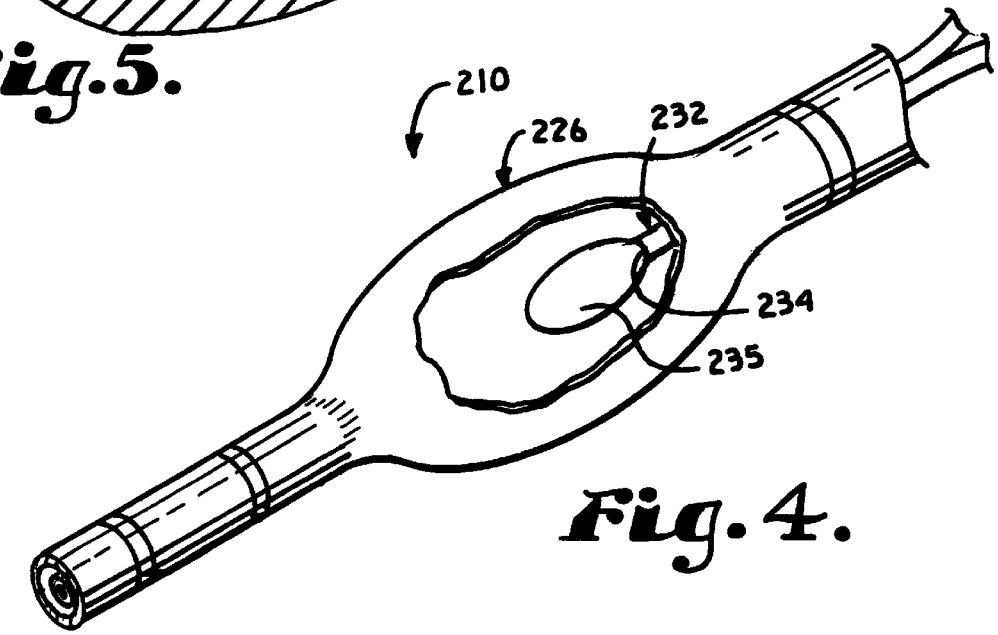
FIG. 4 is an enlarged partial perspective view of an alternate embodiment of a catheter, with parts broken away showing a lumen diaphragm disposed within a catheter terminal port region.

Still another embodiment of the catheter system 210, depicted in FIG. 4 is similar in all respects except that the distal lumen aperture 234 disposed within the terminal port region 226 is equipped with a diaphragm 235. The diaphragm 235 may be constructed of any suitable nontoxic elastomeric material.

A catheter in accordance with the present invention is shown in FIG. 5 in position in the airway of a patient 42. The catheter is introduced through one of the nares 44, and extends into and through the patient's nasal cavity 46, nasopharynx 48, oropharynx 50 and past the epiglottic cartilage 52 to the laryngopharynx 54.

In operation in the airway of a patient 42 during a sleep cycle, narrowing or occlusion of a portion of the airway by a region of soft tissue during an apneic event causes a gaseous volumetric pressure changes to traverse the apertures 28 of the adjacent terminal port region 26. The pressure drop is communicated through a respective lumen aperture 34 to a lumen 24 and via the lumen to the respective pressure transducer 14. In embodiments having a diaphragm 235, the pressure drop is communicated via displacement of the diaphragm or by a pressure change of a gas such as air, within the diaphragm. Advantageously, in this embodiment the diaphragm 235 will be displaced even when the terminal port apertures 228 or the diaphragm covering the lumen aperture 234 are occluded by secretions.

In this manner, one or more occluded regions of the airway can be identified with particularity despite the presence of obstructive secretions, and many obstructive events at multiple locations can be recorded, without the need for manipulation of the cannula, which might disrupt the sleep cycle of the patient. Pressure measurements from the various transducers 14 may also be correlated in order to produce a profile of obstructions and their severity along the length of the catheter 12. This information may be used by the diagnostician to determine the location of the areas of greatest concern for sequencing of treatment.

A syringe 38 communicates via a syringe port 38 with each obstructed lumen 24, to permit introduction of a dye 40 into the lumen. Application of an injection force to syringe 38 either during or following an obstructive event forces the dye 40 through the lumen aperture 34, and outwardly through the terminal port apertures 28 into the obstructive tissue, where it serves to demarcate the area of obstructive tissue for surgical excision. Embodiments having a diaphragm 235, may include in the diaphragm one or more small apertures in the diaphragm 235 to permit passage of the dye 40 across the diaphragm 235, out into the terminal port region 226, and into the obstructive tissue.

A method of locating an obstruction in the airway of a patient in accordance with the present invention broadly includes the steps of (a) providing a diagnostic catheter system 10 having proximal and distal ends 22,20 and an elongate tubular outer wall 18 having a plurality of perforate terminal port regions 26 and circumscribing a plurality of lumens 24, each lumen having a distal end 32 in fluid communication with one of the perforate terminal poet regions 26, and a proximal end 36, (b) inserting the distal end 20 of the catheter into the upper airway of a patient 42, and (c) coupling a pressure transducer 14 with each of the lumen distal ends 36 and sensing a pressure change in one of the lumens 24. The method may also include the additional step of injecting a dye 40 into the lumen proximal end 36, through the lumen distal end 32, and outwardly through a catheter perforate region 26 to mark the obstructive soft tissue for surgical removal by various methods.

What is claimed and desired to be secured by Letters Patent is as follows:

1. A catheter for insertion into the airway of a patient for locating an obstruction and comprising:

a) walls forming a plurality of elongated lumens extending in parallel relation from a respective proximal end to a respective distal end of each lumen;

b) an elongated tubular outer wall encasing said walls forming said lumen;

c) a plurality of perforate regions spaced along said outer wall, each perforate region having a plurality of perforations formed through said outer wall; and d) each lumen having gas pressure communicated thereto at an aperture at a selected location therealong through said perforations at a respective one of said perforate regions for measurement in such a manner that indications of substantially instantaneous gas pressures existing respectively at said perforate regions are obtained and provide a determination of a location of an obstruction in said airway.

2. The apparatus as set forth in claim 1, further including:

a) each lumen having a respective pressure sensor fluidically communicating therewith at a proximal end thereof for measuring a gas pressure in the respective lumen.

3. The apparatus as set forth in claim 1, further including:

a) a syringe coupled with said proximal end of an obstructed lumen for injecting a dye into said lumen proximal end, through said lumen aperture and outwardly through said perforations for contacting and marking the obstruction.

4. The apparatus as set forth in claim 1, wherein said outer wall is integrally coupled with said lumen walls.

5. The apparatus as set forth in claim 1, wherein said lumen walls are in spaced relationship to each other.

6. The apparatus as set forth in claim 1, wherein said lumen aperture is located at a distal end thereof.

7. The apparatus as set forth in claim 1, further including a diaphragm coupled with each of said lumen apertures.

8. The apparatus as set forth in claim 1, said outer wall further including a radiopaque marker.

9. A catheter system for insertion into the airway of a patient for locating obstructions therein, and comprising:

a) walls forming a plurality of elongated lumens extending in parallel relation from a respective proximal end to a respective distal end of each lumen;

b) an elongated tubular outer wall encasing said walls forming said lumens;

c) a plurality of perforate regions spaced along said outer wall, each perforate region having a plurality of perforations formed through said outer wall;

d) each lumen having gas pressure communicated thereto at an aperture at a selected location therealong through said perforations at a respective one of said perforate regions; and e) each lumen having a respective pressure sensor fluidically communicating therewith at a proximal end thereof and measuring a gas pressure in the respective lumen in such a manner that indications of substantially instantaneous gas pressures existing respectively at said perforate regions are obtained and provide a determination of an obstruction in said airway.

10. The system as set forth in claim 9, further including:

a) a syringe coupled with said proximal end of an obstructed lumen for injecting a dye into said lumen proximal end, through said lumen aperture and outwardly through said perforations for contacting and marking the obstruction.

11. The system as set forth in claim 9, further including a diaphragm coupled with each of said lumen apertures.

12. The apparatus as set forth in claim 9, wherein said lumen aperture is located at a distal end thereof.

13. The apparatus as set forth in claim 9, said outer wall further including a radiopaque marker.

14. In a catheter assembly for insertion into the airway of a patient for locating an obstruction and having walls forming a plurality of lumens, each lumen having a proximal and a distal end and a tubular outer wall encasing said lumen walls, the improvement comprising:

a) a plurality of perforate regions spaced along said outer wall, each perforate region having a plurality of perforations formed through said outer wall;

b) each lumen having gas pressure communicated thereto at an aperture at a selected location therealong through said perforations at a respective one of said perforate regions; and c) each lumen having a respective pressure sensor fluidically communicating therewith at a proximal end thereof and measuring a gas pressure in the respective lumen in such a manner that indications of substantially instantaneous gas pressures existing respectively at said perforate regions are obtained and provide a determination of a location of an obstruction in said airway.

15. The apparatus as set forth in claim 14, further including:

a) a syringe coupled with said lumen proximal end of an obstructed lumen for injecting a dye into the lumen, through said lumen aperture, and outwardly through said catheter perforations for contacting and marking the obstruction.

16. The apparatus as set forth in claim 14, further including a diaphragm coupled with each of said lumen apertures.

17. The apparatus as set forth in claim 14, wherein said lumen aperture is located at a distal end thereof.

18. The apparatus as set forth in claim 14, the outer wall further including a radiopaque marker.

19. A method of locating an obstruction in the airway of a patient and comprising:

a) providing a catheter having walls forming a plurality of elongated lumens extending in parallel relation from a respective proximal end to a respective distal end of each lumen, an elongated tubular outer wall encasing said walls forming said lumens, a plurality of perforate regions spaced along said outer wall, each perforate region having a plurality of perforations formed through said outer wall, each lumen having gas pressure communicated thereto at an aperture at a selected location therealong through said perforations at a respective one of said perforate regions;

b) inserting said catheter into the airway of a patient; and c) coupling a pressure sensor with each of said lumen proximal ends and sensing a pressure change in one of said lumens.

20. The method as set forth in claim 19, further including the step of:

a) injecting a dye into said lumen proximal end, though said lumen aperture and outwardly through said catheter perforations for contacting and marking said obstruction.

21. The method as set forth in claim 19, said catheter further including a diaphragm coupled with each of said distal apertures.

22. The method as set forth in claim 19, wherein said lumen aperture is located at a distal end thereof.

23. The method as set forth in claim 19, said outer wall further including a radiopaque marker.

* * * * *